United States Patent
Suzuki et al.

(10) Patent No.: US 11,679,282 B2
(45) Date of Patent: Jun. 20, 2023

(54) TREATMENT SYSTEM

(71) Applicant: OLYMPUS CORPORATION, Hachioji (JP)

(72) Inventors: Tatsuya Suzuki, Koganei (JP); Hideo Sanai, Hachioji (JP); Masaya Ota, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 923 days.

(21) Appl. No.: 16/598,272

(22) Filed: Oct. 10, 2019

(65) Prior Publication Data

US 2020/0038693 A1 Feb. 6, 2020

Related U.S. Application Data

(63) Continuation of application No. PCT/JP2017/015008, filed on Apr. 12, 2017.

(51) Int. Cl.
*A61B 18/08* (2006.01)
*A61B 18/12* (2006.01)
(Continued)

(52) U.S. Cl.
CPC .............. *A61N 7/00* (2013.01); *A61B 18/08* (2013.01); *A61B 18/12* (2013.01); *H01H 36/00* (2013.01);
(Continued)

(58) Field of Classification Search
CPC .......... A61N 7/00; A61B 18/08; A61B 18/12; A61B 2017/00367; A61B 2017/00876;
(Continued)

(56) References Cited

U.S. PATENT DOCUMENTS

| | | | |
|---|---|---|---|
| 2003/0199794 A1 | 10/2003 | Sakurai et al. | |
| 2008/0255413 A1* | 10/2008 | Zemlok | A61B 17/1155 600/106 |
| 2018/0036004 A1* | 2/2018 | Collings | A61B 17/07207 |

FOREIGN PATENT DOCUMENTS

| | | |
|---|---|---|
| JP | 2002-260495 A | 9/2002 |
| JP | 2003-305050 A | 10/2003 |
| WO | 2016/067739 A1 | 5/2016 |

OTHER PUBLICATIONS

Oct. 15, 2019 Translation of International Preliminary Report on Patentability issued in International Patent Application No. PCT/JP2017/015008.

(Continued)

*Primary Examiner* — Ahmed M Farah
*Assistant Examiner* — Sebastian X Lukjan
(74) *Attorney, Agent, or Firm* — Oliff PLC

(57) ABSTRACT

A treatment system can include a treatment instrument with an operation input element that has a magnet; and a sensor that detects a parameter that changes with a movement of the magnet together with the operation input element based on an operation of the operation input element. The treatment system can also include a control apparatus that can control the supply of electrical energy to the treatment instrument for operation of the treatment instrument. The control apparatus includes a processor that can determine a relationship between a change in a distance between the sensor and the magnet and a change in the parameter, and to set, based on the relationship, a threshold for switching between an ON state and an OFF state of the supply of the electrical energy to the treatment instrument.

8 Claims, 10 Drawing Sheets

(51) Int. Cl.
  *H01H 36/00* (2006.01)
  *A61B 17/00* (2006.01)
  *A61B 18/00* (2006.01)
  *A61N 7/00* (2006.01)

(52) U.S. Cl.
  CPC .............. *A61B 2017/00367* (2013.01); *A61B 2017/00876* (2013.01); *A61B 2018/00184* (2013.01)

(58) Field of Classification Search
  CPC ...... A61B 2018/00184; A61B 18/1402; A61B 18/1206; A61B 2017/00075; A61B 17/320068; A61B 18/14; A61B 2017/00017; A61B 2017/00115; A61B 2017/00123; A61B 2017/00464; A61B 2017/00473; A61B 2017/00482; A61B 2017/00725; A61B 2018/00666; A61B 2018/00708; A61B 2018/00898; A61B 2018/0094; A61B 2018/00988; A61B 2018/00994; A61B 2018/167; A61B 2090/061; A61B 2090/0808; H01H 36/00; H03K 17/972; H03K 2217/94026
  See application file for complete search history.

(56) References Cited

OTHER PUBLICATIONS

Jun. 10, 2022 Office Action issued in Chinese Patent Application No. 201780089535.2.
Mar. 2, 2022 Office Action issued in Chinese Patent Application No. 201780089535.2.
Jun. 20, 2017 International Search Report issued in International Patent Application No. PCT/JP2017/015008.

* cited by examiner

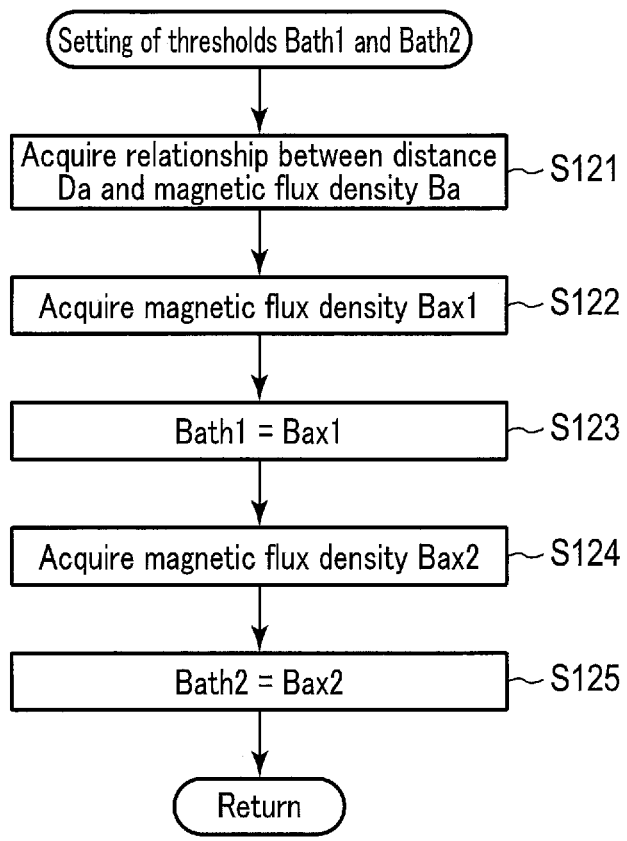
F I G. 10

TREATMENT SYSTEM

CROSS-REFERENCE TO RELATED APPLICATIONS

This is a Continuation Application of PCT Application No. PCT/JP2017/015008, filed Apr. 12, 2017, the entire contents of which are incorporated herein by reference.

The present application relates generally to a treatment system that includes a control apparatus that controls supply of electrical energy to a treatment instrument based on a magnetic flux density of a sensor.

BACKGROUND

A treatment instrument and a control apparatus can control a supply of electrical energy to the treatment instrument. The treatment instrument can be provided with an operation input element such as a button, and the operation input element includes a magnet. The treatment instrument can also be provided with a sensor such as a Hall element for detecting a magnetic flux density. As the operation input element moves based on an operation of the operation input element, a distance between the magnet and the sensor changes, and a magnetic flux density of the sensor changes. The control apparatus supplies the treatment instrument with electrical energy for operating the treatment instrument based on the switching of the magnetic flux density of the sensor, from a state of being equal to or lower than a first threshold to a state of being greater than the first threshold, by the operation of the operation input element. As the electrical energy is supplied to the treatment instrument, an end effector applies treatment energy, such as a high-frequency current and/or ultrasonic vibration, to a treatment target to treat the treatment target. Also, the control apparatus stops supplying the treatment instrument with the electrical energy for operating the treatment instrument, based on the switching of the magnetic flux density of the sensor from a state of being equal to or greater than a second threshold to a state of being lower than the second threshold by the operation of the operation input element. In such a treatment instrument, each of the first threshold and the second threshold is set to a fixed value.

SUMMARY

According to exemplary embodiments, a treatment system includes a treatment instrument including an operation input element including a magnet; and a sensor configured to detect a parameter that changes with a movement of the magnet together with the operation input element based on an operation of the operation input element, and a control apparatus configured to control supply of electrical energy to the treatment instrument for operation of the treatment instrument. The control apparatus includes a processor configured to acquire a relationship between a change in a distance between the sensor and the magnet and the parameter, and to set, based on the relationship, a threshold for switching between an ON state and an OFF state of the supply of the electrical energy to the treatment instrument.

Advantages will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10 is a flowchart showing a process performed by the processor of an exemplary embodiment in setting a threshold for switching a state of supply of the electrical energy to the treatment instrument with respect to a magnetic flux density of a sensor.

DETAILED DESCRIPTION

Figure 1:
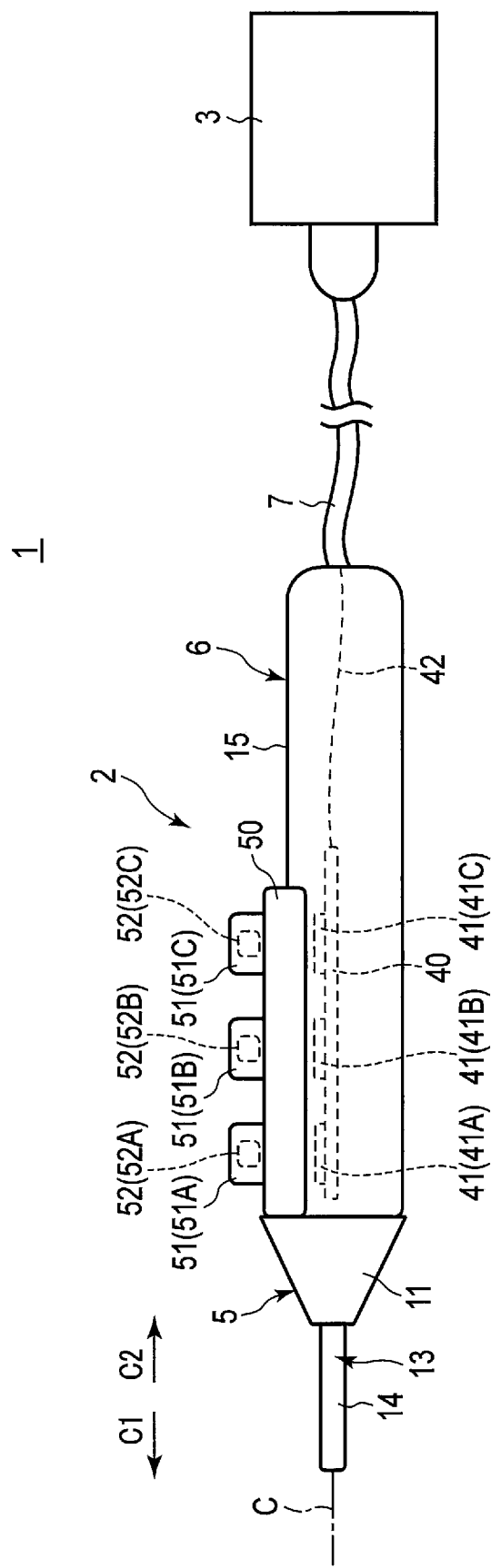
FIG. 1 schematically shows a treatment system according to an exemplary embodiment.

FIG. 1 shows a treatment system 1 which uses an energy source apparatus 3 as a control apparatus of the present embodiment. As shown in FIG. 1, the treatment system 1 includes a treatment instrument 2 and the energy source apparatus 3. The energy source apparatus 3 controls the supply of electrical energy to the treatment instrument 2 for operation of the treatment instrument 2. The treatment instrument 2 includes a holdable first connection member (housing) 5 and a second connection member (support member) 6 separately attached to the first connection member 5. One end of a cable 7 is connected to the second connection member 6. The other end of the cable 7 is connected to the energy source apparatus 3.

In one example, the first connection member (first connection body) 5 is discarded after use of the treatment instrument 2. After the use of the treatment instrument 2, the second connection member (second connection body) 6 is cleaned and sterilized, etc. for reuse. One end of the cable 7 is connected to the second connection member 6. The other end of the cable 7 is separately connected to the energy source apparatus 3.

The second connection member 6 includes a holdable housing 15. The housing 15 has a longitudinal axis C as a central axis, and extends along the longitudinal axis C. One side along the longitudinal axis C is defined as a distal side (arrow C1 side), and a side opposite to the distal side is defined as a proximal side (arrow C2 side).

The first connection member 5 includes a case 11, forming an exterior, and an end effector 14. The end effector 14 performs treatment on a treatment target such as a living tissue. The first connection member (distal side connection member) 5 is attached to a distal end of the second connection member (proximal side connection member) 6 from the distal side. In the present embodiment, a rod member (probe) 13 is attached to the case 11 so as to protrude from a distal end of the case 11 to the distal side. The end effector 14 is formed by the protruding portion of the rod member (probe) 13 from the case 11.

Figure 2:
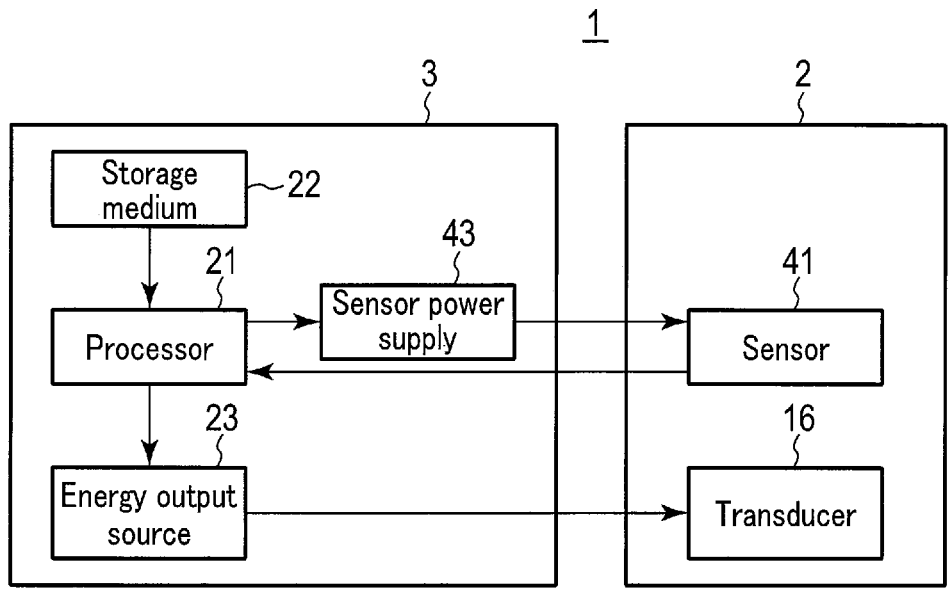
FIG. 2 is a block diagram schematically showing an electrical connection state in the treatment system according to an exemplary embodiment.

FIG. 2 is a block diagram showing a control configuration in the treatment system 1. As shown in FIG. 2, the energy source apparatus 3 includes a processor (controller) 21 that controls the entire treatment system 1 and a storage medium (memory) 22. The processor 21 is formed of an integrated circuit including a central processing unit (CPU), an application specific integrated circuit (ASIC), a field programmable gate array (FPGA), and the like. The processor 21 may be formed of a single integrated circuit or a plurality of integrated circuits. Processing by the processor 21 is performed in accordance with a program stored in the processor 21 or the storage medium 22. Also, the storage medium 22 stores a processing program used by the processor 21, and parameters and tables, etc., used in computing by the processor 21. In one example, the processor 21 is provided in the treatment instrument 2, and at least a part of the processing described later is performed by the processor 21 provided in the treatment instrument 2. In this case, the processor 21 provided in the treatment instrument 2 also forms the control apparatus that controls the supply of the electrical energy to the treatment instrument 2 for operating the treatment instrument 2. Further, in this case, the treatment instrument 2 may be provided with the storage medium 22.

An ultrasonic transducer 16 is provided inside the housing 15 of the second connection member 6. The ultrasonic transducer 16 generates ultrasonic vibration by converting electrical energy into vibrational energy. With the second connection member 6 attached to the first connection member 5, a proximal end of the rod member 13, forming the end effector 14, and a distal end of the ultrasonic transducer 16 are connected to each other inside the housing 15. Therefore, with the second connection member 6 attached to the first connection member 5, the ultrasonic vibration generated by the ultrasonic transducer 16 is transmitted to the end effector 14 via the rod member 13.

The energy source apparatus 3 includes an energy output source 23 as an output source that outputs electrical energy for operating the treatment instrument 2. The energy output source 23 is connected to the treatment instrument 2 via an electrical path (not shown). The electrical path is formed, for example, of electrical wiring or the like extending inside the cable 7. The energy output source 23 includes a waveform generator, a conversion circuit, a transformer, and the like, and converts power from a battery power source, an outlet power source, or the like into, for example, alternating-current power of any frequency within a predetermined frequency range. The energy output source 23 outputs the alternating-current power through the electrical path, and supplies the alternating-current power to the ultrasonic transducer 16 as the electrical energy for operating the treatment instrument 2. The ultrasonic vibration generated by the ultrasonic transducer 16 is transmitted to the end effector 14 via the rod member 13, and applied, as treatment energy, from the end effector 14 to a treatment target.

In one example, a high-frequency current is used as treatment energy instead of the ultrasonic vibration. In this case, the end effector 14 is provided with an electrode having conductivity. In addition, a counter electrode plate attached to a subject (human body) is electrically connected to the energy output source 23. The energy output source 23 supplies high-frequency power to the electrode of the end effector 14 and the counter electrode plate, as the electrical energy for operating the treatment instrument 2. Thereby, the electrode and the counter electrode plate function as electrodes having different potentials, and a high-frequency current flows between the end effector 14 and the counter electrode plate through the treatment target. The high-frequency current is applied to the treatment target.

In another example, heat generated by a heater is used as treatment energy. In this case, the end effector 14 is provided with a heater, and the energy output source 23 supplies direct-current power or alternating-current power to the heater as the electrical energy for operating the treatment instrument 2. As the electrical energy is supplied to the heater, heat by the heater is applied to the treatment target.

The processor 21 controls the supply of the electrical energy to the treatment instrument 2, for operating the treatment instrument 2, by controlling the output from the energy output source 23. The treatment instrument 2 is supplied with electrical energy to thereby apply at least one of the aforementioned ultrasonic vibration, high-frequency energy, or heat to the treatment target as treatment energy. For example, ultrasonic vibration and high-frequency energy may be simultaneously applied to the treatment target; or high-frequency energy and heat may be simultaneously applied to the treatment target.

As shown in FIGS. 1 to 3B, a substrate 40, such as a flexible substrate, is provided inside the housing 15 of the second connection member 6. A sensor 41 (three sensors 41A to 41C in the present embodiment) is provided on the substrate 40. Each of the sensors 41 is, for example, a Hall element, and detects a magnetic flux density B (Ba; Bb; Bc). The number of sensors 41 is not limited to three, as long as at least one sensor 41 is provided. The sensor 41 is electrically connected to the processor 21 of the energy source apparatus 3 via an electrical path 42. Also, the energy source apparatus 3 is provided with a sensor power supply 43 that outputs a current (electrical energy) for operating the sensor 41. The sensor 41 is electrically connected to the sensor power supply 43 via the electrical path 42. The output of the current from the sensor power supply 43 to the sensor 41 is controlled by the processor 21 or the like. The electrical path 42 is formed by a plurality of electrical wires extending through the inside of the housing 15 and the inside of the cable 7, an electrical circuit on the substrate 40, and the like.

Figure 4:
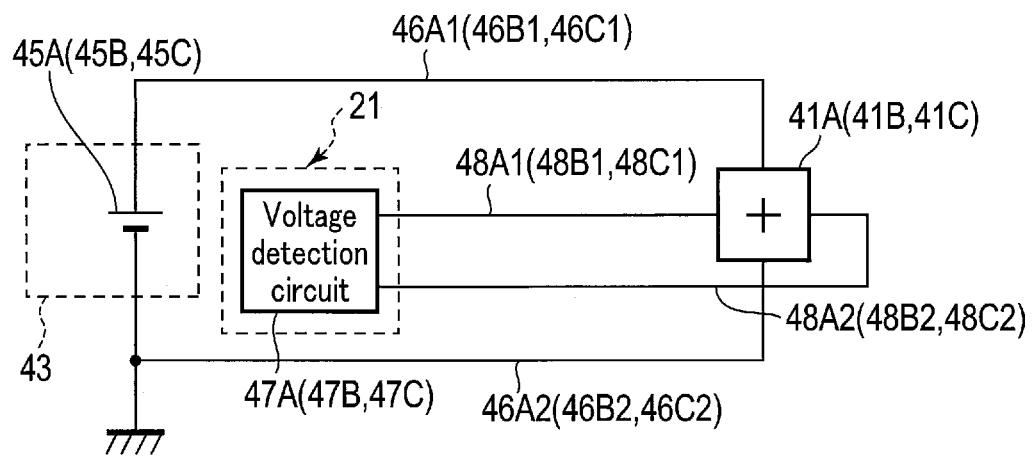
FIG. 4 schematically shows a state of electrical connection of a sensor to a processor and a sensor power supply according to an exemplary embodiment.

FIG. 4 shows a state of electrical connection of one of the sensors 41 (41A in FIG. 4) to the processor 21 and the sensor power supply 43. As shown in FIG. 4, the sensor power supply 43 includes a power supply 45A that outputs a current for operating the sensor 41A. The power supply 45A is, for example, a direct-current power supply. The sensor 41A is electrically connected to the power supply 45A via current paths 46A1 and 46A2 (that form a part of the electrical path 42). The processor 21 also includes a voltage detection circuit 47A. The sensor 41A is electrically connected to the voltage detection circuit 47A via sensor output paths 48A1 and 48A2 (that form a part of the electrical path 42). In one example, the voltage detection circuit 47A may be provided separately from the processor 21.

In the present embodiment, the processor 21 uses the Hall effect produced by the sensor 41A, which is a Hall element or the like, to obtain a magnetic flux density Ba detected by the sensor 41A. That is, the processor 21 causes the power supply 45A of the sensor power supply 43 to output a current, and causes the current to flow to the sensor 41A through the current paths 46A1 and 46A2, to thereby operate the sensor 41A. When the sensor 41A is in operation, generation of a magnetic field in a direction perpendicular to the current passing through the current paths 46A1 and 46A2 causes an electromotive force to be generated in the direction perpendicular to the current and in a direction perpendicular to the magnetic field, via the Hall effect. The generation of the electromotive force causes the sensor 41A to output electrical energy (voltage) to the sensor output paths 48A1 and 48A2, and a voltage is applied between the sensor output paths 48A1 and 48A2. The voltage detection circuit 47A detects the voltage between the sensor output paths 48A1 and 48A2. In this context, the voltage between the sensor output paths 48A1 and 48A2 changes in accordance with the magnetic flux density Ba of the magnetic field of the sensor 41A, and the voltage is larger as the magnetic flux density Ba is larger. Therefore, the voltage detection circuit 47A of the processor 21 acquires the voltage between the sensor output paths 48A1 and 48A2 as output information from the sensor 41A that changes in accordance with the magnetic flux density Ba. Also, the storage medium 22 stores a table, a function, or the like that shows a relationship concerning the voltage between the sensor output paths 48A1 and 48A2 and the magnetic flux density Ba. The processor 21 calculates the magnetic flux density Ba of the sensor 41A based on the result of the detection by the voltage detection circuit 47A, the relationship between the voltage and the magnetic flux density Ba stored, and the like.

Each of the sensors 41B and 41C other than the sensor 41A is also electrically connected to the processor 21 and the sensor power supply 43 in a manner similar to the sensor 41A. Therefore, the treatment system 1 includes a power supply (45B; 45C) similar to the power supply 45A, a current path (46B1, 46B2; 46C1, 46C2) similar to the current paths 46A1 and 46A2, a voltage detection circuit (47B; 47C) similar to the voltage detection circuit 47A, and a sensor output path (48B1, 48B2; 48C1, 48C2) similar to the sensor output paths 48A1 and 48A2. The processor 21 acquires the magnetic flux density Bb of the sensor 41B and a magnetic flux density Bc of the sensor 41C in a manner similar to the magnetic flux density Ba of the sensor 41A. In one example, the sensors 41A to 41C may be provided electrically in parallel, and a common power supply provided to the sensor power supply 43 may output a current for operating the sensors 41A to 41C to the sensors 41A to 41C.

The first connection member 5 is provided with a protruding piece 50 that protrudes from the case 11 toward the proximal side. As an operation input element, an operation button 51 (three operation buttons 51A to 51C in the present embodiment) is movably attached to the protruding piece 50. An operation to output the electrical energy for operating the treatment instrument 2 from the energy source apparatus 3 (energy output source 23) is input into each of the operation buttons 51. In the present embodiment, the number of operation buttons 51 is the same as the number of sensors 41. Each of the operation buttons 51 is provided to correspond to one of the sensors 41. Also, each of the operation buttons 51 includes a magnet 52 for generating a magnetic field. Each of the magnets 52 (52A to 52C in the present embodiment) is fixed to the corresponding operation button (one of the operation buttons 51 corresponding thereto) and is movable relative to the protruding piece 50 together with the corresponding operation button (one of the operation buttons 51 corresponding thereto). Each of the operation buttons 51 moves together with the corresponding magnet (one of the magnets 52 corresponding thereto) when the operation is input.

Each of the sensors 41 is disposed opposite to the corresponding operation button (one of the operation buttons 51 corresponding thereto) and the corresponding magnet (one of the magnets 52 corresponding thereto). Also, a distance D (Da; Db; Dc) between each of the sensors 41 and the corresponding magnet (one of the magnets 52 corresponding thereto) is changed by the movement of the corresponding operation button (one of the operation buttons 51 corresponding thereto). In each of the sensors 41, the magnetic flux density B (Ba; Bb; Bc) is changed by the change of the distance D (Da; Db; Dc) between each of the sensors 41 and the corresponding magnet (one of the magnets 52 corresponding thereto). That is, the magnetic flux density B is a parameter that changes with a movement of the magnet together with the operation input element. That is, in each of the sensors 41, the magnetic flux density B (Ba; Bb; Bc) is changed by the movement of the corresponding operation button (one of the operation buttons 51 corresponding thereto).

Figure 3A:
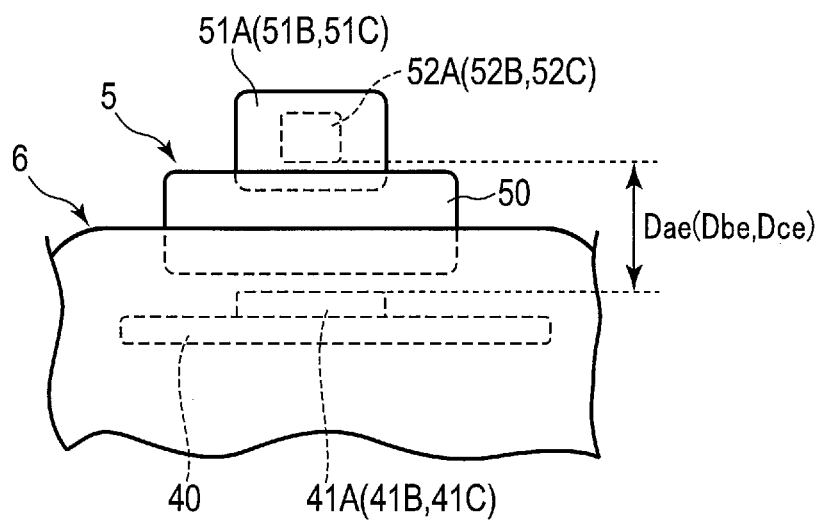
FIG. 3A schematically shows a state in which an operation button is at an initial position according to an exemplary embodiment.

Each of the operation buttons 51 is located at an initial position Pe (Pae; Pbe; Pce) when no operation input is performed, that is, when the operation buttons 51 are not pressed. FIG. 3A shows a state in which one of the operation buttons 51 (51A in FIG. 3A) is located at the initial position Pe (Pae in this example). As shown in FIG. 3A, when the operation button 51A is located at the initial position Pae, the operation button 51A (magnet 52A) is located at a position farthest from the sensor 41A within a range of movement relative to the sensor 41A. Therefore, when the operation button 51A is located at the initial position Pae, a distance Dae between the sensor 41A and the corresponding magnet 52A is the greatest distance Da between the sensor 41A and the magnet 52A to be found within the range of the movement of the operation button 51A.

Figure 3B:
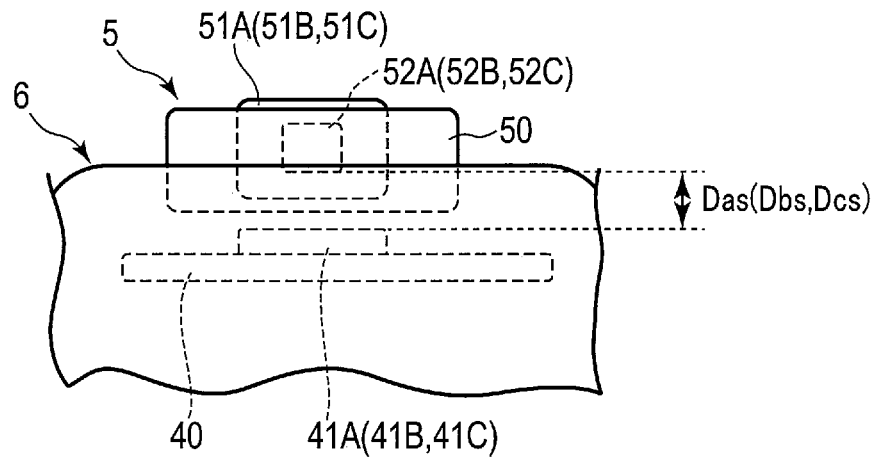
FIG. 3B schematically shows a state in which an operation button is at a pushed position according to an exemplary embodiment.

FIG. 3B shows a state in which one of the operation buttons 51 (51A in FIG. 3B) is most fully pushed into the protruding piece 50. As shown in FIG. 3B, in the state where the operation button 51A is most fully pushed in, the operation button 51A is located at a pushed position (maximum displacement position) Pas. The operation button 51A is movable between the initial position Pae and the pushed position Pas. When the operation button 51A is located at the pushed position Pas, the operation button 51A (magnet 52A) is closest to the sensor 41A within the range of the movement relative to the sensor 41A. Therefore, when the operation button 51A is located at the pushed position Pas, a distance Das between the sensor 41A and the magnet 52A is the smallest distance Da between the sensor 41A and the magnet 52A within the range of the movement of the operation button 51A.

The operation button 51B is also movable between the initial position Pbe and a pushed position Pbs in a manner similar to the operation button 51A. The operation button 51C is also movable between the initial position Pce and a pushed position Pcs in a manner similar to the operation button 51A.

In the present embodiment, the processor 21 acquires the magnetic flux density Be of the sensor 41 in the state where the corresponding operation button (one of 51) is located at the initial position Pe, as a relationship between the distance D and the magnetic flux density B. Based on the acquired relationship (magnetic flux density Be), the processor 21 sets: a threshold (first threshold) Bth1 for switching from a state (OFF state), where the electrical energy for operating the treatment instrument 2 is not supplied from the energy source apparatus 3 to the treatment instrument 2, to a state (ON state), where the electrical energy for operating the treatment instrument 2 is supplied from the energy source apparatus 3 to the treatment instrument 2; and a threshold (second threshold) Bth2 for switching from the state (ON state), where the electrical energy for operating the treatment instrument 2 is supplied from the energy source apparatus 3 to the treatment instrument 2, to the state (OFF state), where the electrical energy for operating the treatment instrument 2 is not supplied from the energy source apparatus 3 to the treatment instrument 2.

Next, the operation and effects of the energy source apparatus 3, which is a control apparatus, and the treatment system 1 will be described. When treating a treatment target using the treatment system 1, the second connection member 6 is connected to the energy source apparatus 3 via the cable 7. A current is supplied from the sensor power supply 43 to each of the sensors 41 to operate the sensors 41. Also, the connection members 5 and 6 are connected to each other. The end effector 14 is disposed near the treatment target.

At any timing (time point) from a time when the connection members 5 and 6 are connected to a time when the end effector 14 is brought into contact with the treatment target, the thresholds Bth (Bth1 and Bth2), for switching between the ON state where the electrical energy for operating the treatment instrument 2 is supplied to the treatment instrument 2 and the OFF state where the electrical energy for operating the treatment instrument 2 is not supplied to the treatment instrument 2, are set by the processor 21. At this time, the thresholds Bth1 (Bath1; Bbth1; Bcth1) and the thresholds Bth2 (Bath2; Bbth2; Bcth2) are set in each of the sensors 41 (41A to 41C). The thresholds (first thresholds) Bath1, Bbth1, and Bcth1 may be either the same or different from one another. Likewise, the thresholds (second thresholds) Bath2, Bbth2, and Bcth2 may be either the same or different from one another.

Figure 5:
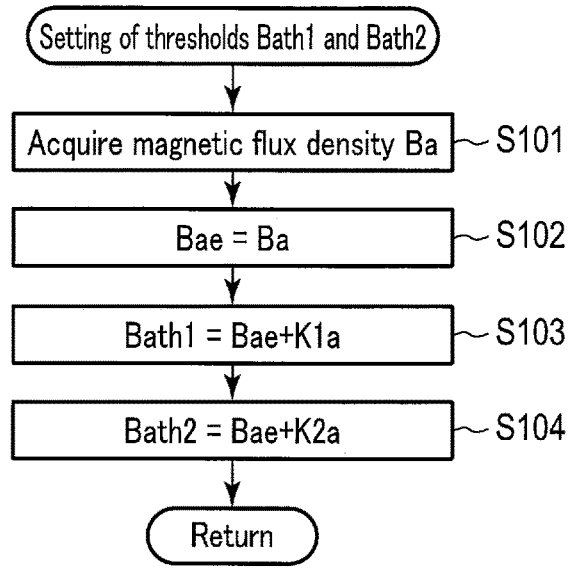
FIG. 5 is a flowchart showing a process performed by the processor of an exemplary embodiment in setting a threshold for switching a state of supply of electrical energy to a treatment instrument with respect to a magnetic flux density of a sensor.

FIG. 5 is a flowchart showing a process performed by the processor 21 in setting the threshold Bth for one of the sensors 41. FIG. 5 shows, as an example, a process performed by the processor 21 when setting the threshold Bath for the sensor 41A. The setting of the threshold Bath shown in FIG. 5 is performed in a state where each of the operation buttons 51 (magnets 52) is located at the initial position Pe, and in a state where the energy source apparatus 3 cannot output the electrical energy for operating the treatment instrument 2. The processor 21 performs the process shown in FIG. 5 for each of the sensors 41, thereby setting, for each of the sensors 41, the first thresholds Bth1 (Bath1 to Bcth1) for switching the state of supply of the electrical energy to the treatment instrument 2 from the OFF state to the ON state, and the second thresholds Bth2 (Bath2 to Bcth2) for switching the state of supply of the electrical energy to the treatment instrument 2 from the ON state to the OFF state.

As shown in FIG. 5, in setting the threshold Bath1 and the threshold Bath2, the processor 21 acquires the magnetic flux density Ba of the sensor 41A (S101). The processor 21 sets the magnetic flux density Ba acquired in S101 as a magnetic flux density Bae of the sensor 41A, in a state where the corresponding operation button 51A is located at the initial position Pae (S102). At this time, the value of the magnetic flux density Ba set as the magnetic flux density Bae may be stored in the storage medium 22.

The processor 21 calculates a value obtained by adding a predetermined value (first value) K1a to the magnetic flux density Bae as the first threshold Bath1 (S103). The processor 21 also calculates a value obtained by adding a predetermined value (second value) K2a to the magnetic flux density Bae as the second threshold Bath2 (S104). The predetermined value K1a is larger than the predetermined value K2a. Therefore, the threshold Bath1 is larger than the threshold Bath2. The difference between the threshold Bath1 and the threshold Bath2 is a value obtained by subtracting K2a from K1a. Also, the predetermined value K1a is set so that the threshold Bath1 is smaller than the magnetic flux density Bas in the state where the operation button 51A is located at the pushed position Pas. The predetermined values K1a and K2a are stored, for example, in the storage medium 22. The predetermined values K1a and K2a are fixed values. The calculated thresholds Bath1 and Bath2 are stored, for example, in the storage medium 22. Thereby, the thresholds Bath1 and Bath2 are set for the sensor 41A. The processor 21 ends the setting of the thresholds Bath1 and Bath2. In a manner similar to the setting of the thresholds Bath1 and Bath2 for the sensor 41A, the processor 21 sets the thresholds Bbth1 and Bbth2 for the sensor 41B and the thresholds Bcth1 and Bcth2 for the sensor 41C.

The processor 21 operates a notification unit such as a lamp, a display screen, or a buzzer based on the completion of the setting of the thresholds Bth1 and Bth2 for each of the sensors 41, and notifies the operator that the setting of the thresholds Bth1 and Bth2 is completed.

When the setting of the thresholds Bth1 and Bth2 is completed for each of the sensors 41, the operator presses one of the operation buttons 51 with the end effector 14 arranged near the treatment target such as a living tissue in the body cavity, and inputs an operation to output electrical energy from the energy source apparatus 3 to the treatment instrument 2. At a point in time when the output of the electrical energy is started, the end effector 14 is located near the treatment target but is not in contact with the treatment target. While the output of the electrical energy from the energy source apparatus 3 is continued, the operator brings the end effector 14 into contact with the treatment target.

In the output control of the electrical energy for operating the treatment instrument 2, the processor 21 acquires the magnetic flux densities B (Ba to Bc) for all the sensors 41 (41A to 41C). At this time, values of the magnetic flux densities Ba to Bc are acquired at the same time with respect to each other. For each of the acquired magnetic flux densities Ba to Bc, the processor determines whether or not the magnetic flux density (one of Ba to Bc) is larger than the corresponding first threshold (one of Bath1 to Bcth1 corresponding thereto). If it is determined that each of the magnetic flux densities Ba to Bc is equal to or less than the corresponding first threshold Bth1, the processor 21 maintains the output of the electrical energy for operating the treatment instrument 2, from the energy source apparatus 3, in a stopped state.

If it is determined that only one of the magnetic flux densities Ba to Bc is larger than the corresponding threshold Bth1, the processor 21 commences the output of the electrical energy for operating the treatment instrument 2, from the energy source apparatus 3, to the treatment instrument 2. That is, the processor 21 causes the energy output source 23 to output the electrical energy, and supplies the electrical energy to the treatment instrument 2. Thereby, at least one of ultrasonic vibration, a high-frequency current, or heat is applied to the treatment target as treatment energy, as described above. That is, the processor 21 supplies the electrical energy for operating the treatment instrument 2 to the treatment instrument 2 when the magnetic flux density B of the corresponding sensor (one of 41 corresponding thereto) is switched from the state of being equal to or less than the first threshold Bth1 to the state of being larger than the first threshold Bth1, by the operation of any one of the operation buttons 51.

At this time, when the magnetic flux density Ba is larger than the threshold Bath1, the processor 21 performs the output in a first output mode. Also, when the magnetic flux density Bb is larger than the threshold Bbth1, the processor 21 performs the output in a second output mode different from the first output mode. If the magnetic flux density Bc is larger than the threshold Bcth1, the processor 21 performs the output in a third output mode which differs from the first output mode and the second output mode. The output state of the electrical energy from the energy source apparatus 3 differs for each of the output modes. That is, the necessity of the output from the energy output source 23 and/or parameters related to the output differ for each of the output modes.

While the output of the electrical energy to the treatment instrument 2 is performed in any of the above-described output modes (e.g., the first output mode), the processor 21 continues the output in the output mode (e.g., the first output mode) in which the output to the treatment instrument 2 is performed, even if the magnetic flux density B (e.g., Bb, Bc) other than the magnetic flux density B (e.g., Ba) corresponding to the output mode changes to be larger than the corresponding threshold (e.g., Bbth1; Bcth1). That is, the processor 21 causes the electrical energy to be output in the output mode corresponding to the magnetic flux density B that has first changed to be larger than the corresponding threshold Bth1 among the magnetic flux densities Ba to Bc.

In one example, if it is determined that two or more of the magnetic flux densities Ba to Bc have simultaneously changed to be larger than the corresponding thresholds Bth1 (Bath1 to Bcth1), the processor 21 performs an error notification. At this time, the output of the electrical energy for operating the treatment instrument 2 from the energy source apparatus 3 is maintained in a stopped state. The processor 21 operates an error notification unit, such as a lamp, a display screen, or a buzzer, to perform an error notification.

The processor 21 determines whether or not the magnetic flux density B (one of Ba to Bc), determined to be larger than the corresponding threshold Bth1, is equal to or less than the corresponding second threshold Bth2 (one of Bath2 to Bcth2 corresponding thereto). If the magnetic flux density B is larger than the corresponding threshold Bth2, the output of the electrical energy for operating the treatment instrument 2, from the energy source apparatus 3, is continued. On the other hand, if the magnetic flux density B is equal to or less than the corresponding threshold Bth2, the processor 21 stops the output of the electrical energy for operating the treatment instrument 2, from the energy source apparatus 3 to the treatment instrument 2. Thereby, the supply of the electrical energy for operating the treatment instrument 2 to the treatment instrument 2 is stopped. That is, the processor 21 stops the supply of the electrical energy for operating the treatment instrument 2 to the treatment instrument 2 when the magnetic flux density B of the corresponding sensor (one of 41 corresponding thereto) is switched from the state of being larger than the second threshold Bth2 to the state of being equal to or less than the second threshold by the operation of one of the operation buttons 51.

Figure 6:
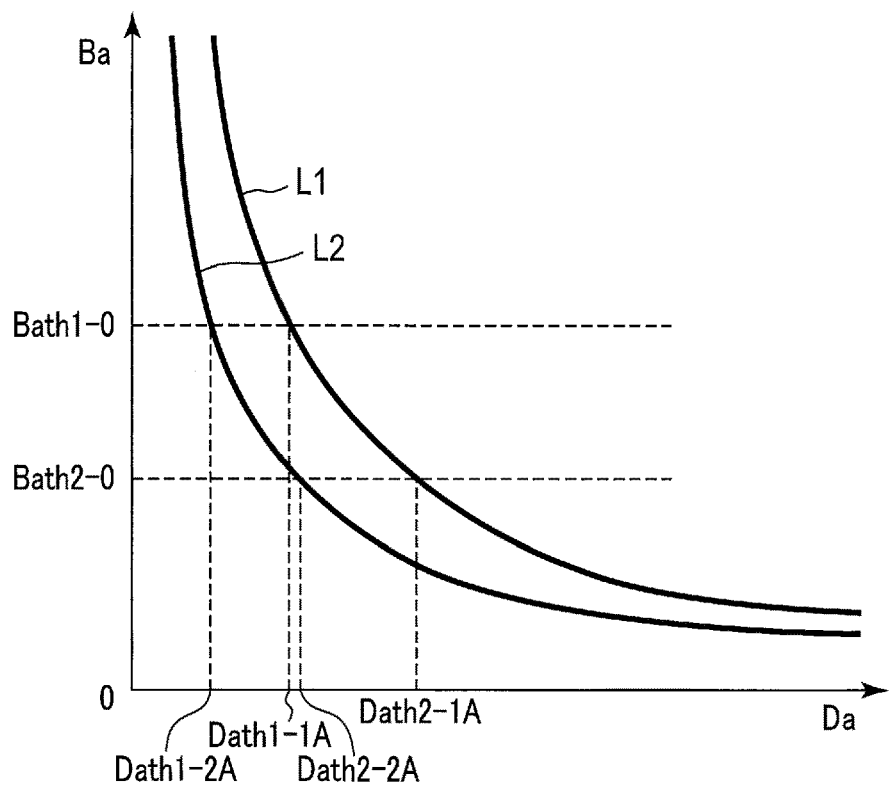
FIG. 6 is a schematic diagram showing a relationship concerning a distance between a magnet and a corresponding sensor and a magnetic flux density of the corresponding sensor according to a comparative example.
Figure 7:
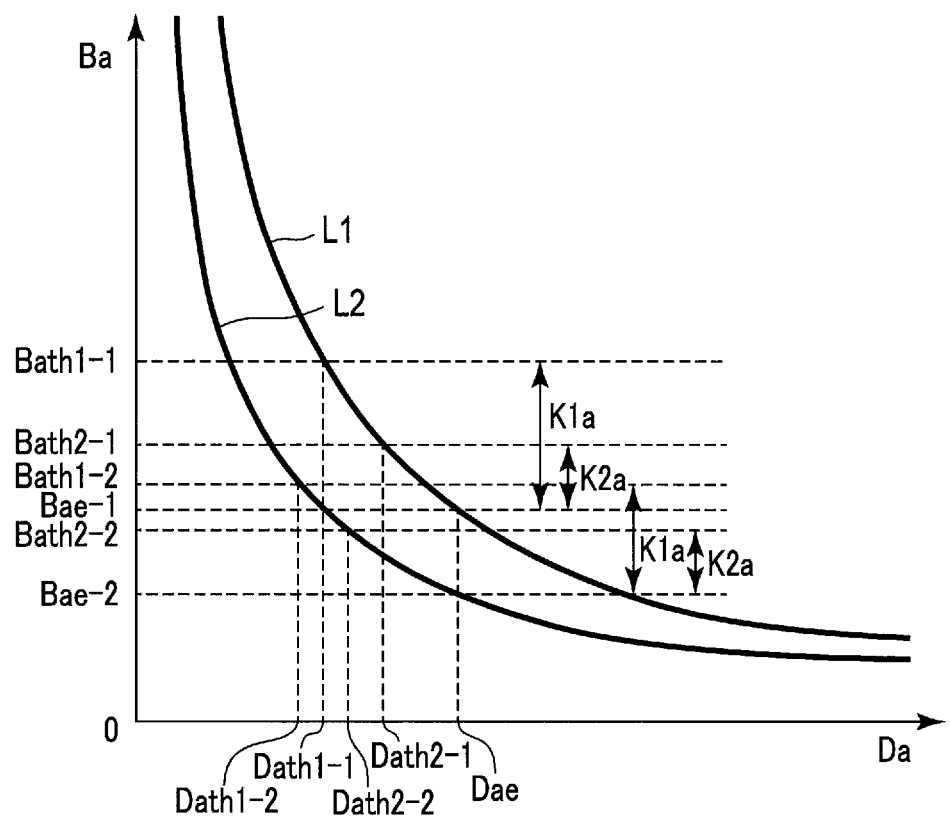
FIG. 7 is a schematic diagram showing a relationship concerning a distance between a magnet and a corresponding sensor and a magnetic flux density of the corresponding sensor according to an exemplary embodiment.

FIGS. 6 and 7 respectively show, with respect to one of the sensors 41, a relationship concerning the distance D between the sensor 41 and the corresponding magnet 52 and the magnetic flux density B of the sensor 41. FIGS. 6 and 7 respectively show, as an example, a relationship concerning the distance Da between the sensor 41A and the magnet 52A and the magnetic flux density Ba of the sensor 41A. In FIGS. 6 and 7, the horizontal axis represents the distance Da, and the vertical axis represents the magnetic flux density Ba.

The relationship between the distance Da and the magnetic flux density Ba may change depending on the individual variability (characteristics) of the sensor 41A, the individual variability (shape and characteristics) of the corresponding magnet 52A, or fluctuating factors such as a shift of an assembly position between the sensor 41A and the magnet 52A. FIGS. 6 and 7 show the relationship for each of the states L1 and L2. The relationship between the distance Da and the magnetic flux density Ba differs between the state L1 and the state L2.

FIG. 6 shows an example, as a comparative example, in which fixed values (Bath1-0, Bath2-0) are used as thresholds for switching the supply state of the electrical energy for operating the treatment instrument 2. That is, in the comparative example shown in FIG. 6, the thresholds Bath1 and Bath2 are constant regardless of the change in the relationship between the distance Da and the magnetic flux density Ba.

In the state L1, the distance Da when the magnetic flux density Ba is equal to the threshold Bath1-0 is defined as a distance Dath1-1A. In the state L2, the distance Da when the magnetic flux density Ba is equal to the threshold Bath1-0 is defined as a distance Dath1-2A. As shown in FIG. 6, the distance Dath1-2A is smaller than the distance Dath1-1A. That is, the distance Dath1 when the magnetic flux density Ba is equal to the threshold Bath1 differs between the state L1 and the state L2. Therefore, as in the comparative example shown in FIG. 6, when the fixed value (Bath1-0) is used for the threshold Bath1, the change in the relationship between the distance Da and the magnetic flux density Ba causes the distance Dath1 to change at the point when the magnetic flux density Ba is equal to the threshold Bath1. As the distance Dath1 changes, so the position of the operation button 51A when the output state of the electrical energy to the treatment instrument 2 is switched changes. The change in the position of the operation button 51A when the output state of the electrical energy to the treatment instrument 2 is switched affects the operability of the operation button 51A.

In the present embodiment, the magnetic flux density Bae is acquired in the processing of S101 and S102. The magnetic flux density Bae in the state where the operation button 51A is located at the initial position Pae changes due to the variation of the relationship between the distance Da and the magnetic flux density Ba. Therefore, the magnetic flux density Bae-1 in the state L1 and the magnetic flux density Bae-2 in the state L2 differ from each other. The processor 21 acquires the magnetic flux density Bae as the relationship between the distance Da and the magnetic flux density Ba.

The threshold Bath1 is calculated by adding a predetermined value (fixed value) K1a to the magnetic flux density Bae in the processing of S103. That is, the processor 21 calculates the threshold Bath1 based on the acquired relationship (magnetic flux density Bae) between the distance Da and the magnetic flux density Ba. Therefore, as shown in FIG. 7, the difference (gap) between a distance Dath1-1, when the magnetic flux density Ba is equal to a threshold Bath1-1 in the state L1, and a distance Dath1-2, when the magnetic flux density Ba is equal to a threshold Bath1-2 in the state L2, is small as compared to the difference between the distance Dath1-1A and the distance Dath1-2A in the comparative example shown in FIG. 6. That is, the change (shift) of the distance Dath1 between the state L1 and the state L2 is small as compared to that of the comparative example shown in FIG. 6. That is, the shift (variation) of the position of the operation button 51A when the supply state of the electrical energy to the treatment instrument 2 switches from the OFF state to the ON state, caused by the variation of the relationship between the distance Da and the magnetic flux density Ba, is small as compared to that of the comparative example shown in FIG. 6.

The threshold Bath2 is calculated by adding a predetermined value (fixed value) K2a to the magnetic flux density Bae in the processing of S104. That is, the threshold Bath2 is calculated based on the acquired relationship (magnetic flux density Bae) between the distance Da and the magnetic flux density Ba, as in the processing for the threshold Bath1. Therefore, as in the case of the threshold Bath1, the shift (variation) of the position of the operation button 51A when the supply state of the electrical energy to the treatment instrument 2 switches from the ON state to the OFF state, caused by the variation of the relationship between the distance Da and the magnetic flux density Ba, is small as compared to that of the comparative example shown in FIG. 6.

With regard to the thresholds Bbth1 and Bbth2 for the sensor 41B and the thresholds Bcth1 and Bcth2 for the sensor 41C as well, the shift (variation) of the position of the operation buttons 51B and 51C, caused by the variation of the relationship between the distances Db, Dc and the magnetic flux densities Bb, Bc, when the supply state of the electrical energy to the treatment instrument 2 switches, is small as compared to that of the comparative example shown in FIG. 6, as in the case of the thresholds Bath1 and Bath2 of the sensor 41A.

In the present embodiment, the change (variation) in the position of the operation button 51 when the supply state of the electrical energy to the treatment instrument 2 is switched, caused by the change in the relationship between the distance D and the magnetic flux density B, is suppressed as described above. Therefore, even if the relationship between the distance D and the magnetic flux density B in the sensor 41 varies (changes) due to, for example, the accuracy of attachment between the connection members 5 and 6 and the temperature of the environment in which the treatment instrument 2 is used, the variation of the position of the operation button 51 when the supply state of the electrical energy to the treatment instrument 2 is switched is suppressed, and the operability of the operation button 51 is secured.

Figure 8:
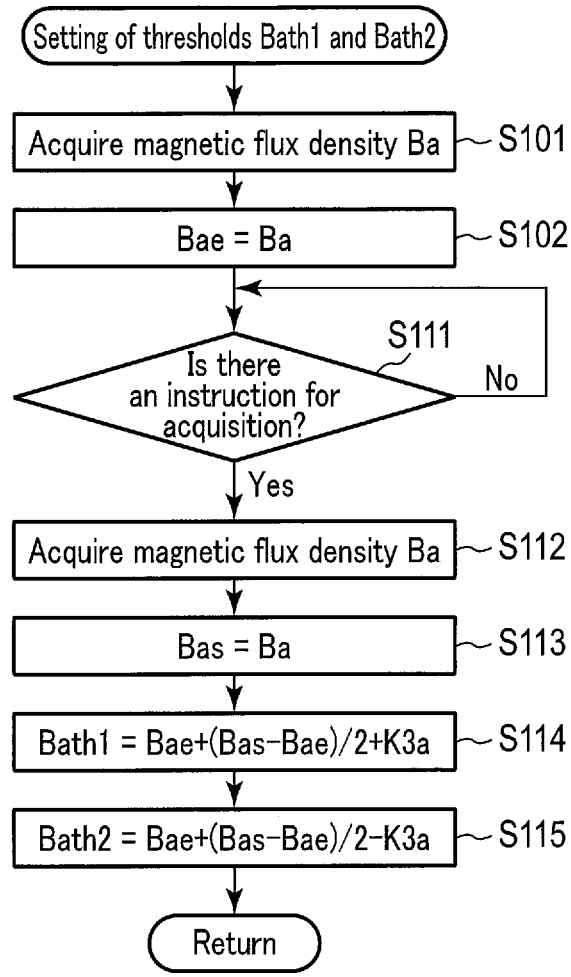
FIG. 8 is a flowchart showing a process performed by the processor of an exemplary embodiment in setting a threshold for switching a state of supply of the electrical energy to the treatment instrument with respect to a magnetic flux density of a sensor.

FIG. 8 is a flowchart showing a process performed by the processor 21 in setting the thresholds Bth1 and Bth2 of the present embodiment. FIG. 8 shows, as an example, a process performed by the processor 21 when setting the thresholds Bath1 and Bath2 corresponding to the sensor 41A. The setting of the thresholds Bath1 and Bath2 shown in FIG. 8 is performed in a state where the electrical energy for operating the treatment instrument 2 cannot be output from the energy source apparatus 3. The processor 21 sets, for each of the sensors 41, the corresponding thresholds Bth1 (one of Bath1 to Bcth1) and Bth2 (one of Bath2 to Bcth2).

The magnetic flux density Ba is acquired in S101. In acquiring the magnetic flux density Ba, the operation button 51A is located at the initial position Pae. In S102, the acquired magnetic flux density Ba is set as the magnetic flux density (first parameter) Bae in the state where the operation button 51A is located at the initial position Pae. The magnetic flux density Ba set as the magnetic flux density Bae may be stored in the storage medium 22. In the present embodiment, the processor 21 determines whether or not an instruction input for acquiring the magnetic flux density Ba has been performed (S111). If the instruction for acquisition is not input (S111—No), the processor 21 waits until it is determined that the instruction for acquisition has been input in S111. The instruction for acquisition is input, for example, at an operation input unit such as a touch panel provided in the energy source apparatus 3.

If the instruction for acquisition is issued (S111—Yes), the processor 21 acquires the magnetic flux density Ba of the sensor 41A (S112). At this time, the magnetic flux density Ba is acquired in the state where the operation button 51A is located at the pushed position Pas. The processor 21 sets the acquired magnetic flux density Ba as the magnetic flux density (second parameter) Bas, in the state where the operation button 51A is located at the pushed position Pas (S113). The magnetic flux density Ba set as the magnetic flux density Bas may be stored in the storage medium 22.

The processor 21 calculates the first threshold Bath1 using the magnetic flux densities Bae and Bas (S114). In S114, the threshold Bath1 is calculated by adding a predetermined value (third value) K3a to an intermediate value between the magnetic flux density Bae and the magnetic flux density Bas. The processor 21 calculates the second threshold Bath2 using the magnetic flux densities Bae and Bas (S115). In S115, the threshold Bath2 is calculated by subtracting the predetermined value (third value) K3a from the intermediate value between the magnetic flux density Bae and the magnetic flux density Bas. The predetermined value K3a is set such that the thresholds Bath1 and Bath2 take values in the range from the magnetic flux density Bae to the magnetic flux density Bas. That is, the difference (2·K3a) between the threshold Bath2 and the threshold Bath1 is smaller than the difference between the magnetic flux density Bas and the magnetic flux density Bae. The predetermined value K3a is stored, for example, in the storage medium 22. The thresholds Bath1 and Bath2 calculated in S114 and S115 are stored, for example, in the storage medium 22. The processor 21 ends the setting of the thresholds Bath1 and Bath2. The processor 21 sets the thresholds Bbth1 and Bbth2 and the thresholds Bcth1 and Bcth2 in a manner similar to the setting of the thresholds Bath1 and Bath2.

Figure 9:
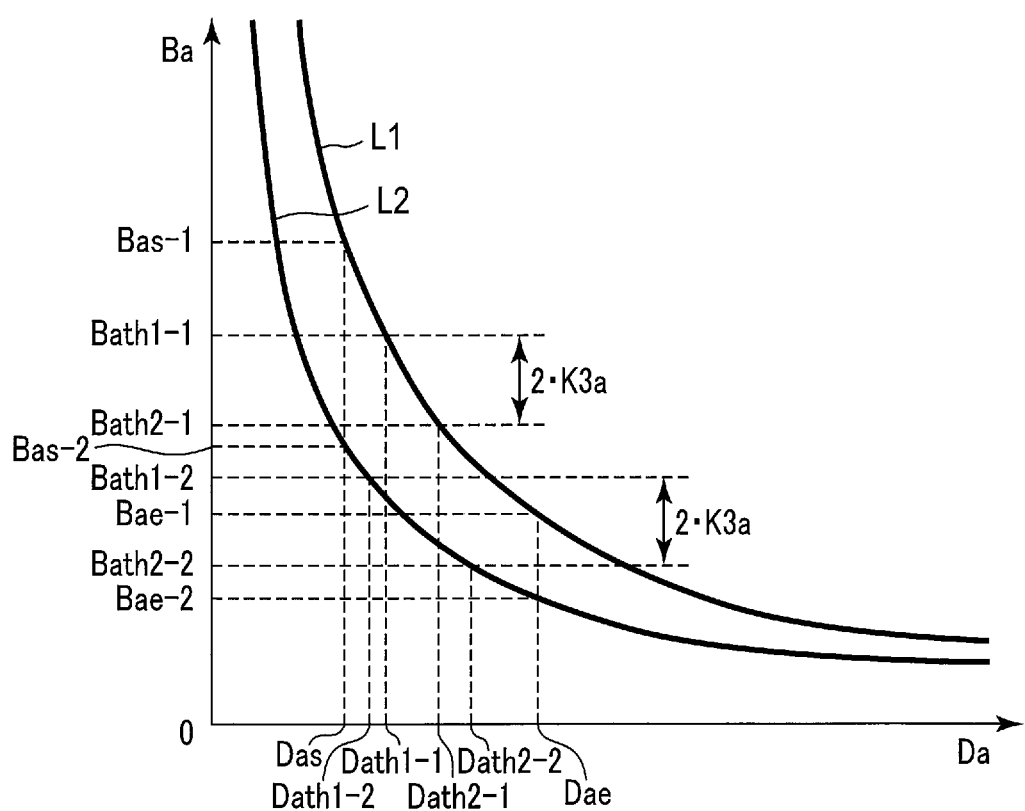
FIG. 9 is a schematic diagram showing a relationship concerning a distance between a magnet and a corresponding sensor and a magnetic flux density of the corresponding sensor according to an exemplary embodiment.

FIG. 9 shows, with respect to one of the sensors 41, a relationship concerning the distance D between the sensor 41 and the corresponding magnet 52 and the magnetic flux density B of the sensor 41. FIG. 9 shows, as an example, a relationship concerning the distance Da between the sensor 41A and the magnet 52A and the magnetic flux density Ba of the sensor 41A. In FIG. 9, the horizontal axis represents the distance Da, and the vertical axis represents the magnetic flux density Ba.

In the present embodiment, the magnetic flux density Bae is acquired in the processing of S101 and S102, and the magnetic flux density Bas is acquired in the processing of S112 and S113. The magnetic flux density Bae, in the state where the operation button 51A is located at the initial position Pae, and the magnetic flux density Bas, in the state where the operation button 51A is located at the pushed position Pas, change due to the variation of the relationship between the distance Da and the magnetic flux density Ba. Therefore, the magnetic flux density Bae-1 in the state L1 and the magnetic flux density Bae-2 in the state L2 differ from each other. Also, the magnetic flux density Bas-1 in the state L1 and the magnetic flux density Bas-2 in the state L2 differ from each other. The processor 21 acquires the magnetic flux densities Bae and Bas as the relationship between the distance Da and the magnetic flux density Ba.

The threshold Bath1 is calculated based on the magnetic flux densities Bae and Bas in the processing of S114. The threshold Bath2 is calculated based on the magnetic flux densities Bae and Bas in the processing of S115. That is, the processor 21 calculates the thresholds Bath1 and Bath2 based on the acquired relationships (magnetic flux densities Bae and Bas) between the distance Da and the magnetic flux density Ba. Therefore, as shown in FIG. 9, the difference (gap) between the distance Dath1-1, when the magnetic flux density Ba is equal to the threshold Bath1-1 in the state L1, and the distance Dath1-2, when the magnetic flux density Ba is equal to the threshold Bath1-2 in the state L2, is small as compared to the difference between the distance Dath1-1A and the distance Dath1-2A of the comparative example shown in FIG. 6. Also, the difference (gap) between the distance Dath2-1, when the magnetic flux density Ba is equal to the threshold Bath2-1 in the state L1, and the distance Dath2-2, when the magnetic flux density Ba is equal to the threshold Bath2-2 in the state L2, is small as compared to the difference between the distance Dath2-1A and the distance Dath2-2A in the comparative example shown in FIG. 6. Therefore, in the present embodiment also, even if the relationship between the distance Da and the magnetic flux density Ba in the sensor 41A varies (changes), the variation of the position of the operation button 51A when the supply state of the electrical energy to the treatment instrument 2 is switched is suppressed, and the operability of the operation button 51A is secured, as in the first embodiment.

Also, in the present embodiment, the predetermined value K3a is set such that the thresholds Bath1 and Bath2 take values in the range from the magnetic flux density Bae to the magnetic flux density Bas. Therefore, the distances Dath1 and Dath2, when the magnetic flux density Ba is equal to the thresholds Bath1 and Bath2, are set in the range from the distance Dae to the distance Das. Therefore, in the present embodiment, the position of the operation button 51A, when the supply state of the electrical energy to the treatment instrument 2 is switched, is securely positioned within the movement range of the operation button 51A, by setting the thresholds Bath1 and Bath2 within the movement range of the operation button 51A from the magnetic flux density Bae to the magnetic flux density Bas.

In a manner similar to the setting of the thresholds Bath1 and Bath2 for the sensor 41A, the processor 21 sets the thresholds Bbth1 and Bbth2 for the sensor 41B and the thresholds Bcth1 and Bcth2 for the sensor 41C. Therefore, the same effect as that for the sensor 41A can be obtained for the sensors 41B and 41C.

(The relationship between the distance D and the magnetic flux density B for each of the sensors 41 can be stored in advance in the storage medium 22 through an inspection test or the like at the time of manufacture.

FIG. 10 is a flowchart showing a process performed by the processor 21 in setting the thresholds Bth1 and Bth2 in the treatment system 1 of the third embodiment. FIG. 10 shows, as an example, a process performed by the processor 21 when setting the thresholds Bath1 and Bath2 corresponding to the sensor 41A. The setting of the threshold Bath shown in FIG. 10 is performed in a state where the electrical energy for operating the treatment instrument 2 cannot be output from the energy source apparatus 3. The processor 21 sets, for each of the sensors 41, the corresponding thresholds Bth1 (one of Bath1 to Bcth1) and Bth2 (one of Bath2 to Bcth2).

The processor 21 acquires a relationship between the distance Da and the magnetic flux density Ba for the sensor 41A from the storage medium 22 (S121). In the present embodiment, the relationship between the distance Da and the magnetic flux density Ba is measured, and the measured relationship is stored in the storage medium 22, for example, at the time of manufacturing the treatment instrument 2. The processor 21 acquires a magnetic flux density Bax1 at a predetermined distance Dax1 based on the acquired relationship (S122). The distance Dax1 is smaller than the distance Dae at the initial position Pae and larger than the distance Das at the pushed position Pae. The distance Dax1 is stored, for example, in the storage medium 22. The processor 21 sets the magnetic flux density Bax1 at the distance Dax1 as the threshold Bath1 (S123).

The processor 21 acquires a magnetic flux density Bax2 at a predetermined distance Dax2 based on the acquired relationship (S124). The distance Dax2 is smaller than the distance Dae at the initial position Pae and larger than the distance Dax1. The distance Dax2 is stored, for example, in the storage medium 22. The processor 21 sets the magnetic flux density Bax2 at the distance Dax2 as the threshold Bath2 (S125).

In the present embodiment, when the operation button 51A moves to a position where the distance Da between the magnet 52A and the sensor 41A is the predetermined distance Dax1 or Dax2, the output state of the electrical energy to the treatment instrument 2 is switched. Therefore, by discretionarily setting the predetermined distances Dax1 and Dax2 stored in the storage medium 22, the position of the operation button 51A when the supply state of the electrical energy to the treatment instrument 2 is switched can be set to a desired position regardless of the relationship between the distance Da and the magnetic flux density Ba.

In an exemplary embodiment, by setting the thresholds Bth1 and Bth2 based on the stored relationship between the distance D and the magnetic flux density B, the change (shift) of the position of the operation button 51A when the supply state of the electrical energy to the treatment instrument 2 is switched, caused by the change in the relationship between the distance D and the magnetic flux density B, can be reliably prevented.

At any timing (time point) from a time when the connection members 5 and 6 are connected to a time when the end effector 14 is brought into contact with the treatment target, the processor 21 identifies the type of the end effector 14 of the first connection member 5. The processor 21 sets parameters related to the output of the electrical energy for operating the treatment instrument 2 based on the type of the end effector 14 identified.

Figure 11:
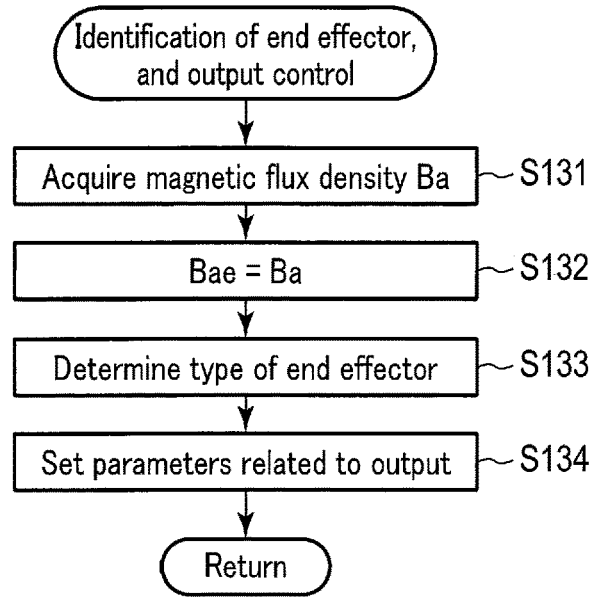
FIG. 11 is a flowchart showing a process performed by the processor of an exemplary embodiment in identifying an end effector and setting an output of the electrical energy to the treatment instrument.

FIG. 11 is a flowchart showing a process performed by the processor 21 in identifying the type of the end effector 14 and setting the parameters related to the output of the electrical energy of the fourth embodiment. The identification of the type of the end effector 14 and the setting of the parameters related to the output are performed in a state where each of the operation buttons 51 is located at the initial position Pe, and in a state where the electrical energy for operating the treatment instrument 2 cannot be output from the energy source apparatus 3.

The processor 21 acquires the magnetic flux density B (corresponding one of Ba to Bc) of a sensor 41 (one of 41A to 41C) (S131). In FIG. 11, for example, the magnetic flux density Ba of the sensor 41A is acquired. The processor 21 sets the acquired magnetic flux density Ba as the magnetic flux density Bae in the state where the operation button 51A is located at the initial position Pae (S132). The magnetic flux density Ba set as the magnetic flux density Bae may be stored in the storage medium 22.

The storage medium 22 also stores a table or the like showing a relationship between the magnetic flux density Bae and the type of the end effector 14. The processor 21 identifies the type of the end effector 14 based on, for example, the magnetic flux density Bae, and the stored relationship between the magnetic flux density Bae and the type of the end effector 14 (S133).

Based on the determination result of the type of the end effector 14 in S133, the processor 21 sets the parameters related to the output of the electrical energy for operating the treatment instrument 2 (S134). The parameters related to the output include, for example, the output level of the electrical energy, the type of treatment energy to be applied to the treatment target, and the threshold for switching between the OFF state and the ON state of the supply of the electrical energy. The processor 21 ends the identification of the type of the end effector 14 and the setting of the parameters related to the output of the electrical energy.

Figure 12:
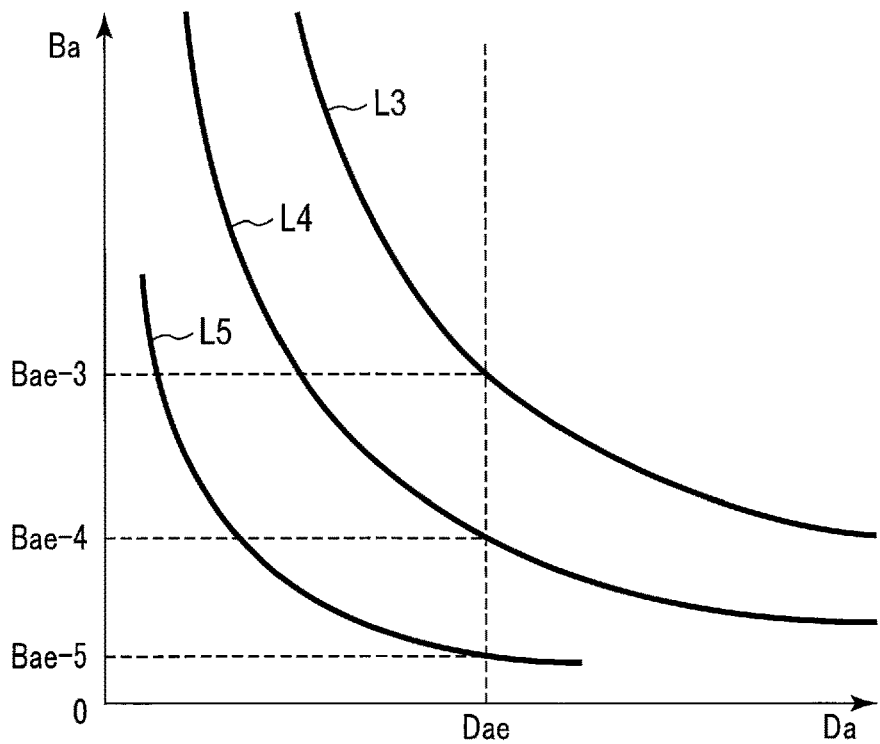
FIG. 12 is a schematic diagram showing a relationship concerning a distance between a magnet and a corresponding sensor and a magnetic flux density of the corresponding sensor according to an exemplary embodiment.

FIG. 12 shows, with respect to one of the sensors 41, a relationship concerning the distance D between the sensor 41 and the corresponding magnet 52 and the magnetic flux density B of the sensor 41. FIG. 12 shows, as an example, a relationship concerning the distance Da between the sensor 41A and the magnet 52A and the magnetic flux density Ba of the sensor 41A. In FIG. 12, the horizontal axis represents the distance Da, and the vertical axis represents the magnetic flux density Ba.

FIG. 12 shows the relationship for each of the states L3 to L5. The type (shape) of the end effector 14 provided to the connection member 5 differs among the states L3 to L5. Also, the intensity of the magnetic field generated by the magnet 52A differs among the states L3 to L5. Therefore, the relationship between the distance Da and the magnetic flux density Ba differs among the states L3 to L5. Accordingly, the magnetic flux densities Bae (Bae-3 to Bae-5) differ among the states L3 to L5.

In an exemplary embodiment, the magnetic flux density Bae is acquired in the processing of S131 and S132. The processor 21 acquires the magnetic flux density Bae as the relationship between the distance Da and the magnetic flux density Ba. In the processing of S133, the type of the end effector 14 is identified based on the acquired relationship (magnetic flux density Bae) between the distance Da and the magnetic flux density Ba. In the processing of S134, the parameters related to the output of the electrical energy supplied to the treatment instrument 2 are set based on the type of the identified end effector 14.

In an exemplary embodiment, the processor 21 performs the output setting suitable for the type (shape) of the end effector 14 provided to the connection member 5, as described above. Therefore, the effort of the operator setting the output mode, etc., according to the type of the end effector 14 is saved.

At any timing (time point) from a time when the connection members 5 and 6 are connected to a time when the end effector 14 is brought into contact with the treatment target, the processor 21 identifies the number and the position of the operation buttons 51 of the first connection member 5. Based on the number and the position of the operation buttons 51, the processor 21 sets the parameters related to the output of the electrical energy for operating the treatment instrument 2.

Figure 13:
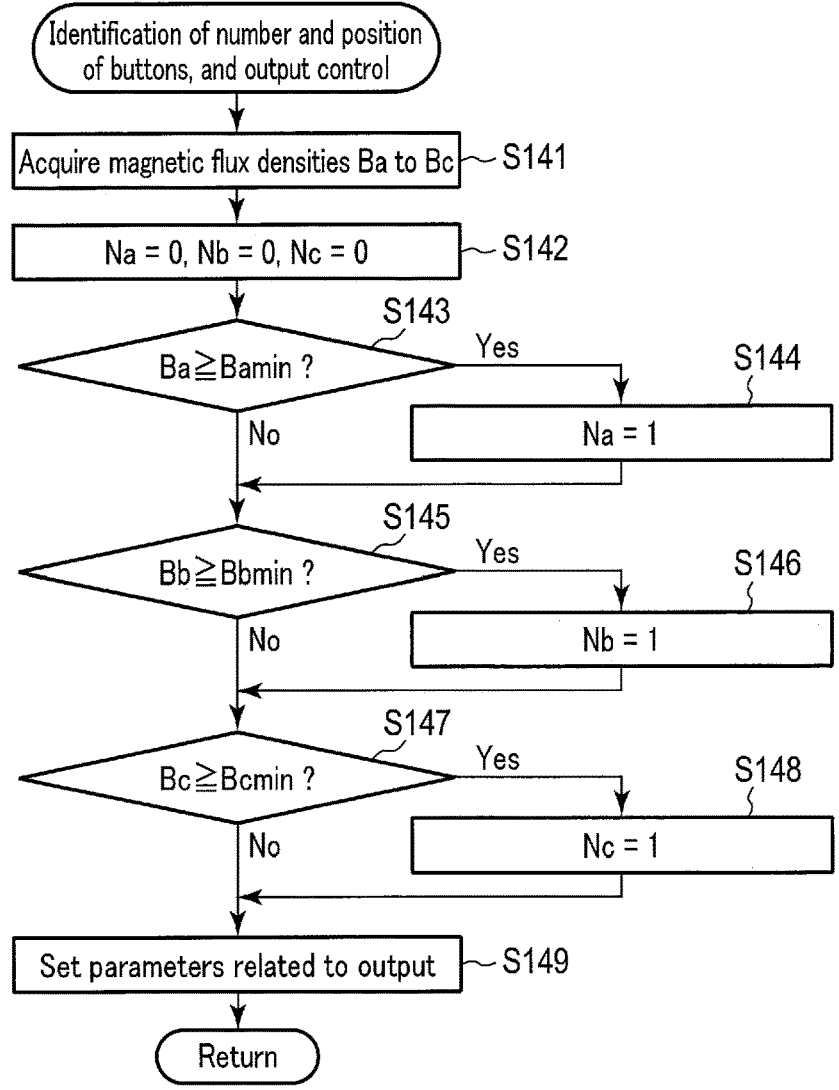
FIG. 13 is a flowchart showing a process performed by the processor of an exemplary embodiment in identifying the number of operation buttons and setting an output of the electrical energy to the treatment instrument.

FIG. 13 is a flowchart showing a process performed by the processor 21 in identifying the number and the position of the operation buttons 51 and setting the parameters related to the output of the electrical energy in the treatment system 1. The identification of the number and the position of the operation buttons 51 and the setting of the parameters related to the output of the electrical energy are performed in a state where the electrical energy for operating the treatment instrument 2 cannot be output from the energy source apparatus 3.

In an exemplary embodiment, the number and the position of the operation buttons 51 are identified based on identifiers Na, Nb, and Nc. The processor 21 acquires the magnetic flux densities B (Ba to Bc) for the respective sensors 41 (41A to 41C) (S141). Also, the processor 21 sets 0 as the identifiers Na, Nb, and Nc (S142). The set identifiers Na, Nb, and Nc may be stored in the storage medium 22.

The processor 21 determines whether or not the magnetic flux density Ba is equal to or greater than a threshold Bamin (S143). If the magnetic flux density Ba is equal to or greater than the threshold Bamin (S143—Yes), the processor 21 sets 1 as the identifier Na of the operation button 51A (S144). The calculated number N of buttons may be stored in the storage medium 22. If the magnetic flux density Ba is smaller than the threshold Bamin (S143—No), the process proceeds to S145, so that the processor 21 performs the processing of S145 and the subsequent processing described later.

The threshold Bamin is set to a value sufficiently smaller than the magnetic flux density Bae in the state where the operation button 51A is located at the initial position Pae. Also, the threshold Bamin is set to a value sufficiently larger than the magnetic flux density Ba in a state where the operation button 51A (the magnet 52A) is not provided at a position facing the sensor 41A. Therefore, when the operation button 51A corresponding to the sensor 41A is provided, the magnetic flux density Ba is larger than the threshold Bamin, and 1 is set as the identifier Na (S144). When the operation button 51A corresponding to the sensor 41A is not provided, the magnetic flux density Ba is smaller than the threshold Bamin, and the identifier Na is maintained at 0 (S143—No).

The processor 21 performs, for each of the magnetic flux densities Bb and Bc, the same processing as that performed in S143 and S144 for the magnetic flux density Ba (S145 to S148). Thus, for each of the sensor 41B and the sensor 41C, it is determined whether or not the operation button 51 is present at the opposing position.

The processor 21 sets the parameters related to the output of the electrical energy for operating the treatment instrument 2 based on the identifiers Na, Nb, Nc set in the processing of S141 to S148 (S149). The processor 21 stores the set parameters in the storage medium 22. The parameters related to the output include, for example, the output level of the electrical energy at the time of the output of the electrical energy, the type of treatment energy to be applied to the treatment target, and the threshold for switching between the OFF state and the ON state of the supply of the electrical energy. The processor 21 ends the identification of the number of buttons and the setting of the parameters related to the output of the electrical energy.

Figure 14:
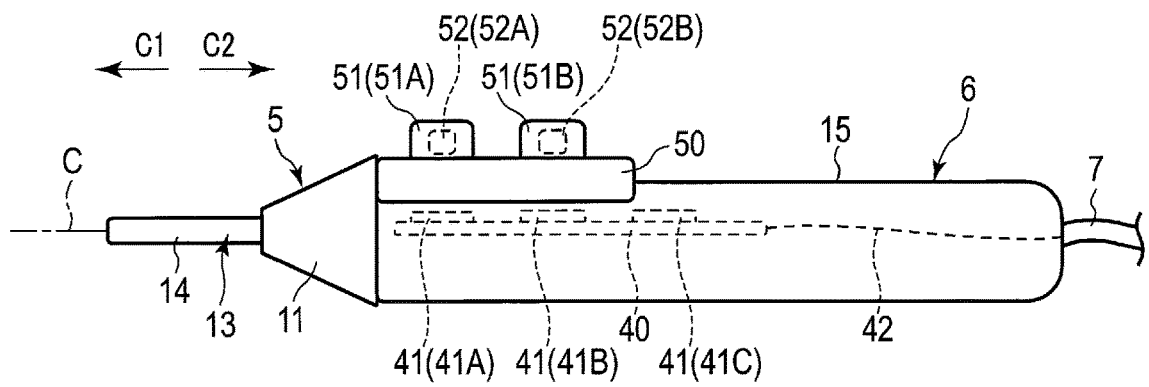
FIG. 14 schematically shows a state in which a first connection member provided with two operation buttons is attached to a second connection member according to an exemplary embodiment.

FIG. 14 shows an example in which the connection member 5 including two operation buttons 51 (51A and 51B) is attached. The second connection member 6 is provided with three sensors 41 (41A to 41C). In the example shown in FIG. 14, the operation button 51A is provided at a position facing the sensor 41A in the state where the connection member 5 is attached. Therefore, the magnetic flux density Ba of the sensor 41A is larger than the threshold Bamin regardless of the position of the operation button 51A. Accordingly, it is determined that the operation button 51A is present in the processing of S143, and 1 is set as the identifier Na in the processing of S144. The identifier Na=1 is stored in the storage medium 22.

In addition, the operation button 51B is provided at a position facing the sensor 41B. Therefore, the magnetic flux density Bb of the sensor 41B is larger than the threshold Bbmin regardless of the position of the operation button 51B. Accordingly, it is determined that the operation button 51B is present in the processing of S145, and 1 is set as the identifier Nb to be added in the processing of S146. The identifier Nb=1 is stored in the storage medium 22.

The operation button 51C is not provided at a position facing the sensor 41C. Therefore, the magnetic flux density Bc of the sensor 41C is smaller than the threshold Bcmin. Thus, in the processing of S147, it is determined that the operation button 51C is not present. Accordingly, the identifier Nc is maintained at 0.

In the processing of S149, parameters related to output control of the electrical energy for operating the treatment instrument 2 are set based on the stored identifiers Na, Nb, and Nc. It is determined that the operation button 51A and the operation button 51B are present, and parameters corresponding to the treatment instrument 2, provided with the two operation buttons 51A and 51B, are set.

In an exemplary embodiment, it is determined whether or not the corresponding operation button 51 is present for each of the sensors 41A to 41C. The parameters related to the output control of the electrical energy for operating the treatment instrument 2 are then set based on at least one of the number, position, combination, or the like of the operation buttons 51. The parameters are set to a state where an output suitable for the determined number, position, combination, etc., of the operation buttons 51 is performed.

In an exemplary embodiment, the processor 21 performs output setting suitable for the number, position, combination, etc., of the operation buttons 51 provided to the connection member 5. Therefore, the effort of the operator setting the output mode, etc., according to the number N of buttons, is saved. In the above-described embodiments, etc., the control apparatus (3) is used with the treatment instrument (2) that includes the operation input element (51) including the magnet (52) and the sensor (41) for detecting the magnetic flux density (B), wherein the magnetic flux density (B) of the sensor (41) changes by the movement of the operation input element (51) together with the magnet (52) based on an operation of the operation input element (51); the control apparatus (3) is configured to control supply of electrical energy for operating the treatment instrument (2) to the treatment instrument (2); and the control apparatus (3) includes the processor (21) configured to acquire a relationship concerning a distance (D) between the sensor (41) and the operation input element (51) and the magnetic flux density (B), and set a threshold (Bth) for switching between an ON state and an OFF state of the supply of the electrical energy based on the relationship.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A treatment system comprising:
a treatment instrument that includes:
an operation input element including a magnet; and
a sensor configured to detect a magnetic flux density that changes when the magnet moves together with the operation input element; and
a control apparatus configured to control a supply of electrical energy to the treatment instrument for operation of the treatment instrument, the control apparatus including:
a processor configured to:
determine a relationship between a change in a distance between the sensor and the magnet and a change in the magnetic flux density; and
based on the relationship, set a threshold for switching between an ON state and an OFF state of the supply of the electrical energy to the treatment instrument, wherein the processor is configured to:
acquire the magnetic flux density of the sensor when the magnet is a furthest distance from the sensor within a movement range of the operation input element relative to the sensor;
set a first threshold at which the supply of the electrical energy to the treatment instrument switches from the OFF state to the ON state by adding a predetermined first value to the magnetic flux density; and
set a second threshold at which the supply of the electrical energy to the treatment instrument switches from the ON state to the OFF state by adding a predetermined second value smaller than the first value to the magnetic flux density.

2. The treatment system according to claim 1, wherein the processor is configured to:
based on the relationship, set a first threshold at which the supply of the electrical energy to the treatment instrument is switched from the OFF state to the ON state, and a second threshold at which the supply of the electrical energy to the treatment instrument is switched from the ON state to the OFF state.

3. The treatment system according to claim 2, wherein the processor is configured to set the first threshold to be larger than the second threshold.

4. The treatment system according to claim 1, further comprising a storage medium configured to store the determined relationship, the processor being configured to acquire the relationship from the storage medium.

5. The treatment system according to claim 1, wherein the processor is configured to acquire the relationship based on output information from the sensor.

6. A treatment system comprising:
a treatment instrument that includes:
   an operation input element including a magnet; and
   a sensor configured to detect a magnetic flux density that changes when the magnet moves together with the operation input element; and
a control apparatus configured to control a supply of electrical energy to the treatment instrument for operation of the treatment instrument, the control apparatus including:
   a processor configured to:
      determine a relationship between a change in a distance between the sensor and the magnet and a change in the magnetic flux density; and
      based on the relationship, set a threshold for switching between an ON state and an OFF state of the supply of the electrical energy to the treatment instrument;
   the processor is configured to acquire a first magnetic flux density of the sensor in a state where the magnet is most distant from the sensor within a movement range of the magnet relative to the sensor, and a second magnetic flux density of the sensor in a state where the magnet is closest to the sensor within the movement range of the magnet relative to the sensor; wherein the processor is configured to:
set a first threshold that is calculated by adding a predetermined value to an intermediate value between the first magnetic flux density and the second magnetic flux density, and at which the supply of the electrical energy to the treatment instrument switches from the OFF state to the ON state; and
set a second threshold which is calculated by subtracting the predetermined value from the intermediate value between the first magnetic flux density and the second magnetic flux density, and at which the supply of the electrical energy to the treatment instrument switches from the ON state to the OFF state.

7. A treatment system comprising:
a treatment instrument that includes:
   an operation input element including a magnet; and
   a sensor configured to detect a magnetic flux density that changes when the magnet moves together with the operation input element; and
a control apparatus configured to control a supply of electrical energy to the treatment instrument for operation of the treatment instrument, the control apparatus including:
   a processor configured to:
      determine a relationship between a change in a distance between the sensor and the magnet and a change in the magnetic flux density; and
      based on the relationship, set a threshold for switching between an ON state and an OFF state of the supply of the electrical energy to the treatment instrument, the treatment instrument used with the processor comprises:
a first connection body comprising the operation input element and an end effector configured to treat a treatment target; and
a second connection body comprising the sensor and separably attached to the first connection body, wherein the processor is configured to determine a type of the end effector based on the relationship, and
set a magnetic flux density related to the supply of the electrical energy to the treatment instrument based on the type of the end effector.

8. The treatment system according to claim 7, wherein:
the sensor further comprises a plurality of sensors; and
the processor is configured to:
   acquire output information from each of the plurality of sensors,
   determine a number of the operation input elements provided to the first connection body based on the output information; and
   set a magnetic flux density related to the supply of the electrical energy to the treatment instrument based on the number of the operation input element.

* * * * *